United States Patent
Zhang et al.

(10) Patent No.: US 9,865,692 B2
(45) Date of Patent: Jan. 9, 2018

(54) SPATIAL TERAHERTZ WAVE PHASE MODULATOR BASED ON HIGH ELECTRON MOBILITY TRANSISTOR

(71) Applicant: University of Electronic Science and Technology of China, Chengdu, Sichuan (CN)

(72) Inventors: Yaxin Zhang, Sichuan (CN); Yuncheng Zhao, Sichuan (CN); Shixiong Liang, Sichuan (CN); Ziqiang Yang, Sichuan (CN)

(73) Assignee: University of Electronic Science and Technology of China, Chungdu, Sichuan Province (CN)

( * ) Notice: Subject to any disclaimer, the term of this patent is extended or adjusted under 35 U.S.C. 154(b) by 0 days.

(21) Appl. No.: 15/587,317

(22) Filed: May 4, 2017

(65) Prior Publication Data
US 2017/0236912 A1    Aug. 17, 2017

(51) Int. Cl.
*H01L 29/15* (2006.01)
*H01L 29/417* (2006.01)
(Continued)

(52) U.S. Cl.
CPC ........ *H01L 29/41758* (2013.01); *H01L 23/66* (2013.01); *H01L 29/2003* (2013.01);
(Continued)

(58) Field of Classification Search
CPC ............... H01L 29/41758; H01L 23/66; H01L 29/2003; H01L 29/205
(Continued)

(56) References Cited

U.S. PATENT DOCUMENTS 9,077,060 B2 *   7/2015   Nguyen .................. H01P 1/127
9,711,697 B2 *   7/2017   Vassant ................... H01L 33/58
(Continued)

OTHER PUBLICATIONS

M. Rahm et al., "THz Wave Modulators: A Brief Review on Different Modulation Techniques", J Infrared Milli Terahz Waves (2013) 34:1-27, Published online: Nov. 9, 2012.*
(Continued)

*Primary Examiner* — Jami M Valentine

(57) ABSTRACT

A spatial terahertz wave phase modulator based on the high electron mobility transistor is provided. The phase modulator combines the quick-response high electron mobility transistor with a novel metamaterial resonant structure, so as to rapidly modulate terahertz wave phases in a free space. The phase modulator includes a semiconductor substrate, an HEMT epitaxial layer, a periodical metamaterial resonant structure and a muff-coupling circuit. A concentration of 2-dimensional electron gas in the HEMT epitaxial layer is controlled through loading voltage signals, so as to change an electromagnetic resonation mode of the metamaterial resonant structure, thereby achieving phase modulation of terahertz waves. The phase modulator has a phase modulation depth of over 90 degrees within a large bandwidth, and a maximum phase modulation depth is about 140 degrees. Furthermore, the phase modulator is simple in structure, easy to machine, high in modulation speed, convenient to use, and easy to package.

9 Claims, 5 Drawing Sheets

(51) Int. Cl.
| | |
|---|---|
| H01L 29/778 | (2006.01) |
| H01L 29/20 | (2006.01) |
| H01L 29/205 | (2006.01) |
| H01L 29/49 | (2006.01) |
| H01L 29/45 | (2006.01) |
| H01L 23/66 | (2006.01) |

(52) U.S. Cl.
CPC .......... *H01L 29/205* (2013.01); *H01L 29/452* (2013.01); *H01L 29/495* (2013.01); *H01L 29/7786* (2013.01); *H01L 2223/6627* (2013.01)

(58) Field of Classification Search
USPC ........................................................ 257/76
See application file for complete search history.

(56) References Cited

U.S. PATENT DOCUMENTS

| | | | | |
|---|---|---|---|---|
| 2005/0162658 | A1* | 7/2005 | Pepper | G01J 3/4338 356/451 |
| 2008/0285606 | A1* | 11/2008 | Kippenberg | G02F 1/39 372/32 |
| 2014/0191188 | A1* | 7/2014 | Vassant | G02F 1/00 257/13 |
| 2016/0233962 | A1* | 8/2016 | Zhang | H04B 10/90 |
| 2017/0108756 | A1* | 4/2017 | Huang | G02F 1/21 |

OTHER PUBLICATIONS

Y. Zhang et al., "Gbps THz external modulator based on high electron mobility transistors-metamaterials," 2015 40th International Conference on Infrared, Millimeter, and Terahertz waves (IRMMW-THz), Hong Kong, 2015, pp. 1-2.Date of Conference Aug. 28, 2015.*

Y. Zhao et al., "Fast THz modulator based on the HEMT-metamaterial," 2016 41st International Conference on Infrared, Millimeter, and Terahertz waves (IRMMW-THz), Copenhagen, 2016, pp. 1-2. Date of conference Sep. 30, 2016.*

Q. Chen et al., "Terahertz metamaterial and its sensing application," 2016 Progress in Electromagnetic Research Symposium (PIERS), Shanghai, 2016, pp. 2392-2392. Date of conference Aug. 11, 2016.*

* cited by examiner

SPATIAL TERAHERTZ WAVE PHASE MODULATOR BASED ON HIGH ELECTRON MOBILITY TRANSISTOR

BACKGROUND OF THE PRESENT INVENTION

Field of Invention

The present invention relates to a field of electromagnetic functional device technology, focusing on a quickly dynamic functional device for a terahertz band.

Description of Related Arts

As one of the key components of the terahertz (THz) communication system, a THz dynamic functional device, namely terahertz external modulator, has becomes the focus of research in the field of THz science and technology. Since terahertz band functional devices required size in micron or nanometer scale, which means microwave and infrared bands devices cannot be applied directly. Therefore, since 2004, Nature/Science and the other top international scientific journals have published many articles about terahertz external modulators, covering a range of combining Si, GaAs, phase-transition, Graphene material systems with metamaterial. By applying external excitation such as temperature changes, light, and electrical field, the THz wave is modulated.

In recent years, with the development of semiconductor materials and technology, High Electron Mobility Transistor (HEMT) have shown excellent performance, and have been successfully applied to detectors, amplifiers, and other areas. HEMT is a novel field effect transistor which applies 2-dimensional electrons gas (2-DEG) in modulation doped heterostructures to work. In 1978, R. Dingle firstly observed high electron mobility. In 1980, Fujitsu developed a HEMT and successfully used it in low noise amplifier. As the third generation of wide bandgap semiconductor material, GaN has not only wide band gap, but also a large thermal conductivity, high electron saturation rate, strong breakdown field and good thermal stability, etc. Therefore, in the preparation of the high-speed functional devices, GaN-based HEMT material has great advantages.

Metamaterial is a kind of artificial electromagnetic array structure, which is made from assemblies of specific geometry resonance units with periodic or aperiodic patterns. The artificial designed structures give them their smart properties capable of manipulating electromagnetic waves to achieve benefits that go beyond what is possible with conventional materials. With the development of modern micro-fabrication techniques, metamaterials played a huge role in the development of passive functional devices, and have developed a variety of related functions devices in millimeter wave, THz, and optical band.

SUMMARY OF THE PRESENT INVENTION

An object of the present invention is to provide a modulator that can quickly and dynamically control phases of the spatially transmitted terahertz waves by applying an external voltage signal, which can effectively and quickly modulate the phase of the spatially transmitted terahertz waves based on design frequency, wherein a phase modulate depth is up to 90 degrees within a large bandwidth.

Accordingly, in order to accomplish the above objects, the present invention provides a metamaterial structure with various resonation modes, and sufficiently combines the HEMT and metamaterial structure together. By utilizing the high-speed dynamic characteristics of the HEMT and the Metamaterials' accurate controlling ability for electromagnetic wave, resonation mode switch of the metamaterial is rapidly controlled based on high electron mobility characteristics of 2-dimensional electrons gas in the HEMT, in such a manner that the phase modulate depth of the HEMT-based terahertz wave phase modulator is up to 90 degrees within the large bandwidth.

Therefore, the present invention provides a high electron mobility transistor-based terahertz wave spatial phase modulator, comprising: a semiconductor substrate; an epitaxial layer on the semiconductor substrate; and a modulation unit array, a positive electrode, as well as a negative electrode on the epitaxial layer; wherein each modulation unit in the modulation unit array comprises: a source resonator, a drain resonator, a gate connector, and a semiconductor doped heterostructure; wherein the drain resonator and the source resonator are structurally identical; comprising: a metal semi-circle and a T-shaped metal feeder; wherein the T-shaped metal feeder comprises a latitudinal branch and a longitudinal branch; the longitudinal branch of the T-shaped metal feeder passes through the metal semi-circle from a top portion thereof; semi-circle openings of the drain resonator and the source resonator face each other and are symmetrically arranged at two sides of the gate connector; the semiconductor doped heterostructure is placed at bottom portions of semi-circle rear ends of the drain resonator and the source resonator, so as to connect the drain resonator and the source resonator; the semiconductor doped heterostructure is also placed at a bottom portion of the gate connector; a row of array elements of the modulation unit array shares the gate connector, and the gate connector of each row is connected to the same negative electrode; the latitudinal branch of the T-shaped metal feeder of the drain resonator of each the modulation unit in a row is connected to the positive electrode in sequence; the latitudinal branch of the T-shaped metal feeder of the source resonator of each the modulation unit in the row is connected to the positive electrode in sequence.

Preferably, rear ends of the drain resonator and the source resonator are connected to the semiconductor doped heterostructure through a metal electrode.

Preferably, a short branch extending towards a circle center is respectively arranged at the semi-circle rear ends of the drain resonator and the source resonator.

Preferably, a portion of the gate connector, which is placed on the semiconductor doped heterostructure, is narrower than other portions of the gate connector.

The semiconductor doped heterostructure are made of AlGaN/GaN, InGaN/GaN, AlGaAs/GaAs, AlGaAs/InGaAs, or AlGaAs/InGaAs/InP, wherein a slash represents combining two materials.

The semiconductor substrate is made of sapphire, high-resistivity silicon, or SiC.

The metal electrode is made of Ti, Al, Ni or Au.

The drain resonator, the source resonator and the T-shaped metal feeder are made of Au, Ag, Cu or Al.

Beneficial effects of the present invention are as follows: (1), the HEMT terahertz phase modulator adopts a two-transistor design, i.e., each modulation unit comprises two high electron mobility transistors, which greatly increases an ability of the HEMT to control an artificial electromagnetic resonant structure, and enhances a resonance strength of the resonant structure, so as to obtain a large phase modulation depth. (2), the HEMT phase modulator uses high electron mobility characteristics of 2-dimensional electrons gas in the HEMT to rapidly control resonation mode switch of the metamaterial, enabling rapid phasing of a spatial transmitted terahertz wave. The resonant structure is well designed for combining the two transistors, in such a manner that the resonant structure has many different resonation modes while the HEMT is switched on or off, and the different resonation modes couples with each other, thereby significantly improving the phase modulation and increasing the modulation bandwidth. (3), the structure has a strong plasticity: while an overall structure of the modulation unit is maintained, a modulation bandwidth size and a modulation frequency band position can be effectively adjusted by changing resonance unit parameters (such as a metal ring radius). Depending on actual needs, a bandwidth of the phase modulator with a modulation depth of up to 90 degrees can be increased to more than 0.2 THz. (4), according to the present invention, the modulation unit array designed by using metamaterial has a 2-dimensional structure, which can be realized by means of micromachining with mature technology and easy manufacture, so as to avoid difficult processing of complex 3-dimensional structures. (5), the present invention provides a transmissive terahertz wave phase modulator, wherein compared to a reflective phase modulator, the device of the present invention is easy to operate and use. Especially, the device plays an effective role during terahertz point-to-point communication. (6), the phase modulator of the present invention provides a modulation depth of about 90 degrees to 140 degrees within a large bandwidth. While having large modulation bandwidth and depth at the same time, the device can also operate at room temperature, normal pressure as well as non-vacuum conditions. The device needs no waveguide loading and is easy to package, which enables a good practical application of the phase modulator.

These and other objectives, features, and advantages of the present invention will become apparent from the following detailed description, the accompanying drawings, and the appended claims.

Figure 1:
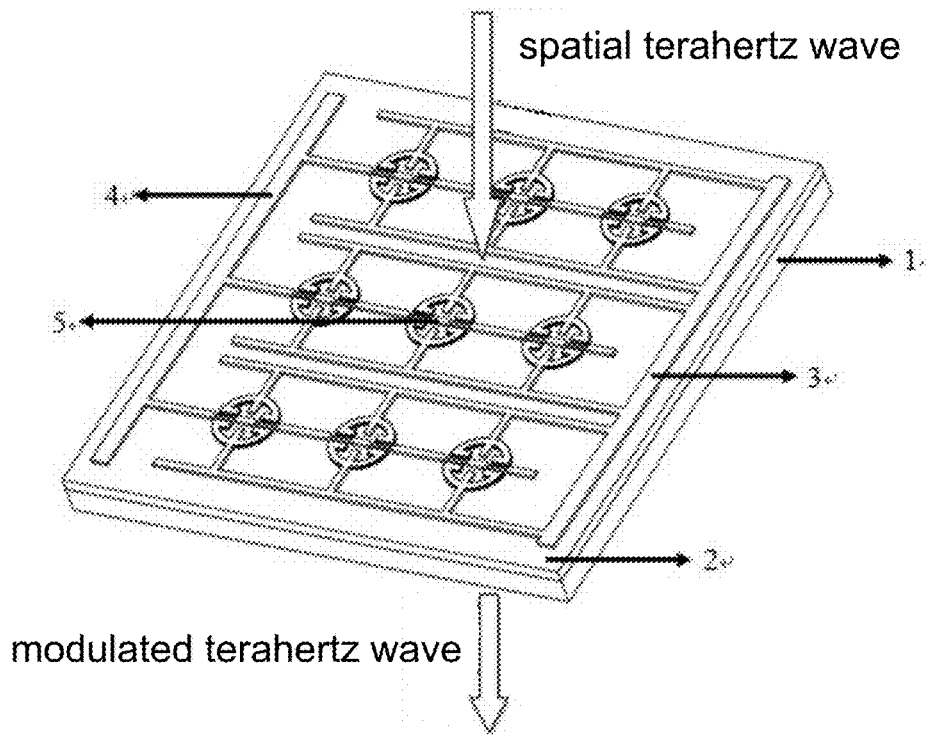
FIG. 1 is an overall sketch view of an HEMT phase modulator according to the present invention.
Figure 2:
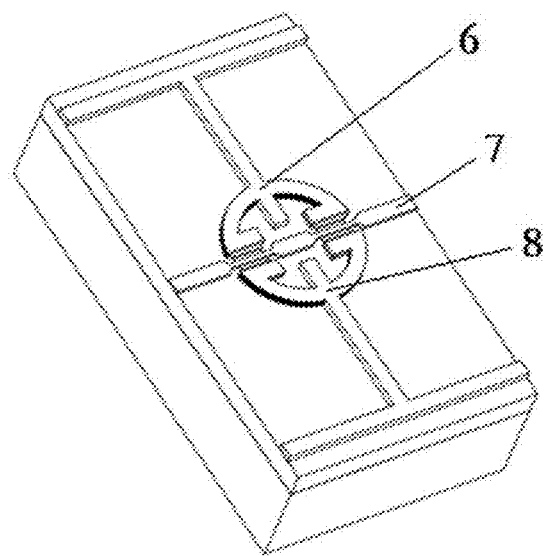
FIG. 2 is a perspective view of a modulation unit of the HEMT phase modulator according to the present invention.
Figure 3:
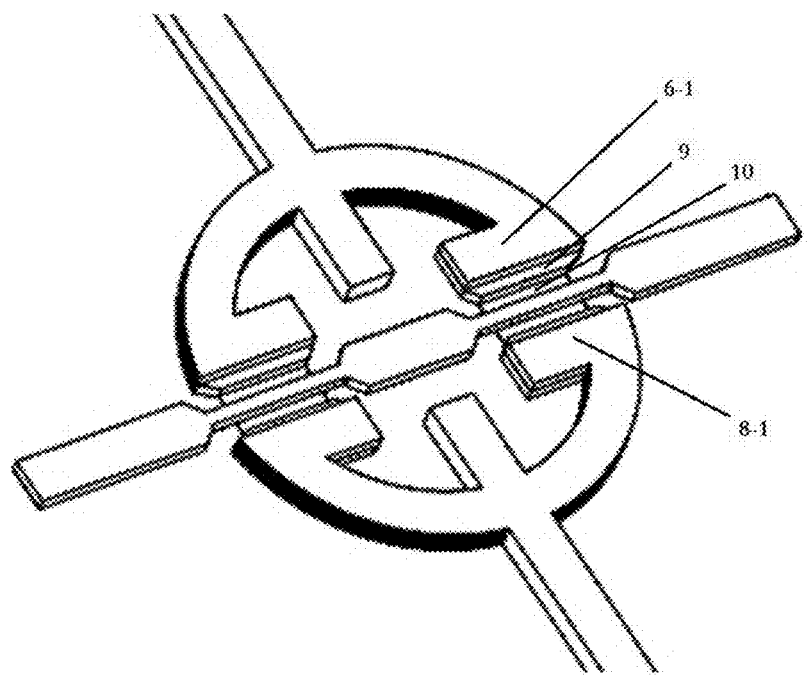
FIG. 3 is a partial view of a resonance unit.
Figure 4:
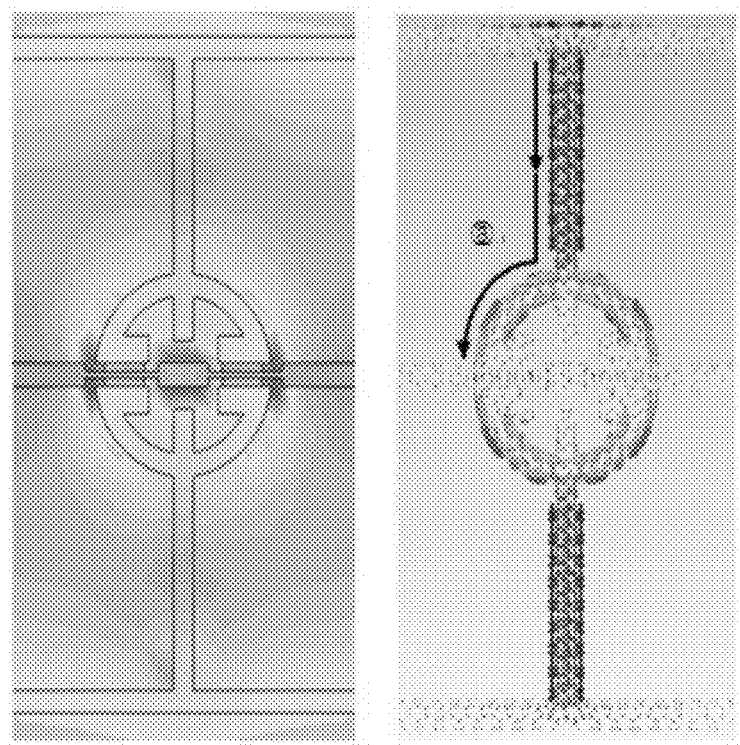
FIG. 4 is a distribution schematic view of a electric field and a surface current of the resonance unit when a voltage is applied.

Element reference: 1. semiconductor; 2. epitaxial layer; 3. positive electrode; 4. negative electrode; 5. modulation unit array; 6. drain resonator; 6-1. rear end of drain resonator; 7. gate connector; 8. source resonator; 8-1. rear end of source resonator; 9. metal electrode; 10. semiconductor doped heterostructure.

DETAILED DESCRIPTION OF THE PREFERRED EMBODIMENT

The present invention sufficiently combines HEMT and metamaterials together to form a triode structure. By utilizing the high-speed dynamic characteristics of the HEMT and the Metamaterials' accurate controlling ability for electromagnetic wave, resonation mode switch of the metamaterial is rapidly controlled based on high electron mobility characteristics of 2-dimensional electrons gas in the HEMT, in such a manner that the phase modulate depth of the HEMT-based terahertz wave phase modulator is up to 90 degrees within the large bandwidth, and rapid and effective phase modulation of spatial transmitted terahertz wave is achieved. According to simulation and experiments, the prevent invention is an HEMT terahertz rapid phase modulator with large phase modulation depth and large modulation bandwidth. Furthermore, the present invention is simple in structure and easy to machine.

The present invention comprises a semiconductor substrate 1, an epitaxial layer 2, a modulation unit array 5, a positive electrode 3 and a negative electrode 4; wherein the epitaxial layer 2 is arranged on the semiconductor substrate 1; the modulation unit array 5, the positive electrode 3 and the negative electrode 4 are arranged on the epitaxial layer 2. The modulation unit array 5 is an M*N array formed by a plurality of modulation units, wherein M>3 and N>3. The modulation unit comprises a high electron mobility transistor and a metamaterial resonant structure. A gate of the transistor is connected to the negative electrode 4, while a source and a drain are connected to the positive electrode 3. The positive electrode 3 comprises a source port for connecting the source of the transistor, and a drain port for connecting the drain of the transistor. Furthermore, the source port and the drain port may be connected to positive electrodes with two different voltages for voltage control between the source and the drain.

Each modulation unit comprises two identical transistors which are symmetrically arranged, and each transistor comprises the source, the gate, the drain, and a heterostructure which are all arranged at an opening of a ring portion of the resonant structure.

The metamaterial resonant unit structure comprises a source resonator, a drain resonator and a gate connector. Each resonant unit comprises a metal ring, wherein two openings at middle-right and middle-left of the metal ring separate the metal ring into an upper semi-ring and a lower semi-ring. An upper metal latitudinal bar and a lower metal latitudinal bar are provided to each of the openings of the metal ring, which contact with an inner side of the metal ring, and are sleeved on the source and the drain of the transistor. The upper and lower metal latitudinal bars are connected to an outer side of the metal ring and extend towards a center portion of the metal ring. Metal strips are arranged at upper and lower sides of the resonant unit and contact with metal strips of adjacent resonant unit. The source resonator comprises a source voltage loader, a metal longitudinal bar and the upper semi-ring. The drain resonator comprises a drain voltage loader, a metal longitudinal bar and the lower semi-ring. The gate connector is placed in a middle of the unit and connects gates of the two transistors in the unit, wherein the gate connector is connected to a gate connector of a left side unit and a right side unit.

The spatial terahertz wave phase modulator based on the high electron mobility transistor of the present invention is composite metal-semiconductor structure formed by the metamaterial resonant structure and the HEMT. Accordingly, the semiconductor substrate is made of sapphire, high-resistivity silicon, or SiC. The epitaxial layer of the HEMT is made of a semiconductor material which is able to form the heterostructure, such as AlGaN/GaN, InGaN/GaN, and AlGaAs/GaAs. Generally, the metal electrode is made of Ti, Al, Ni or Au, and a muff-coupling circuit is made of Au, Ag, Cu or Al. The above metal materials may be replaced by other metal materials with similar features.

Figure 5:
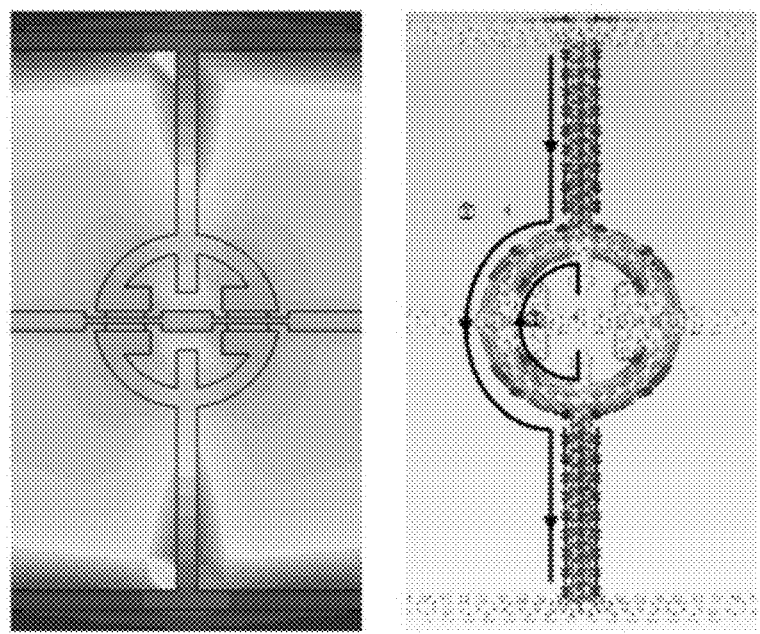
FIG. 5 is a distribution schematic view of a electric field and a surface current of the resonance unit when no voltage is applied.
Figure 6:
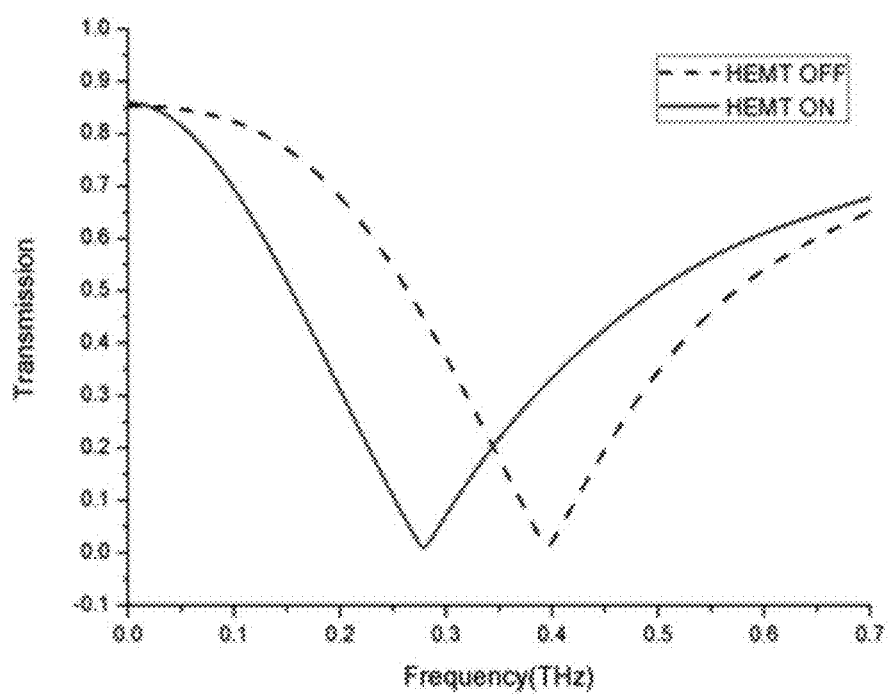
FIG. 6 shows simulation of transmission curves of the HEMT phase modulator with different voltages.
Figure 7:
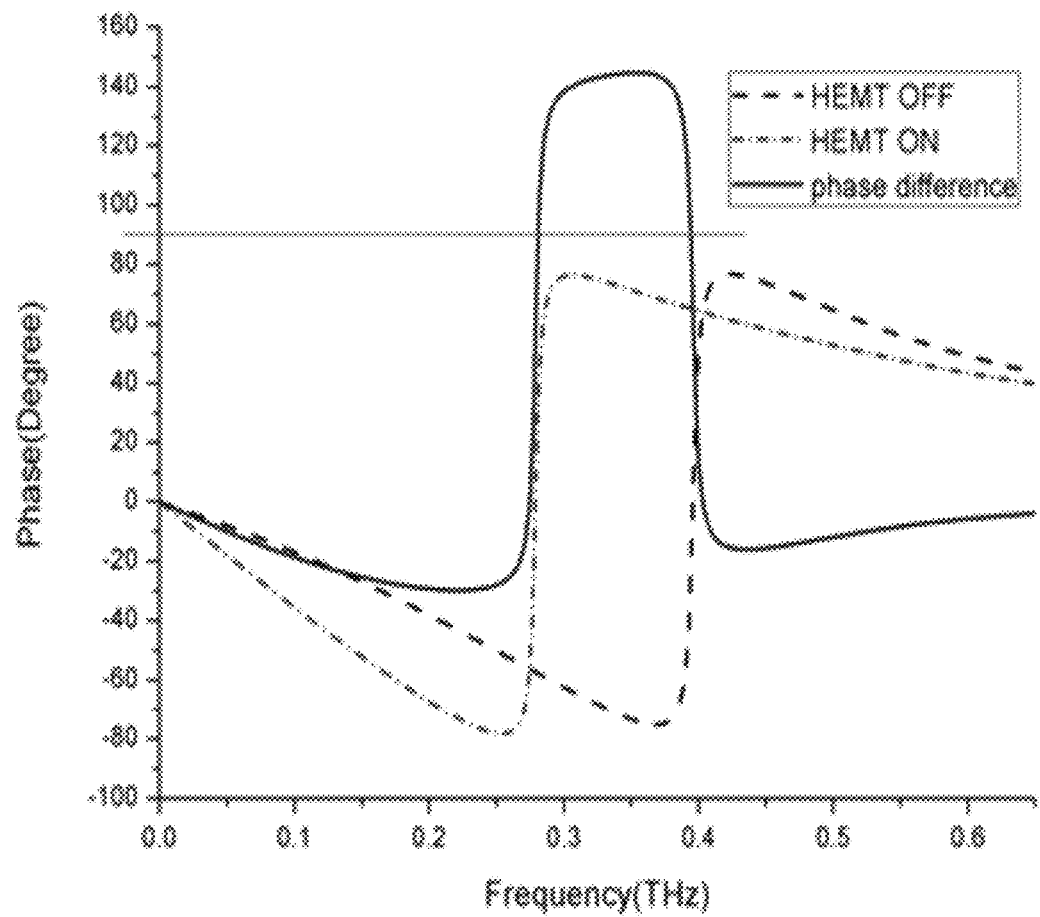
FIG. 7 shows simulation of phase changes of the HEMT phase modulator with different voltages.

The phase modulator uses an external voltage to control a concentration of the 2-dimensional electrons gas in the HEMT, changing the concentration of the 2-dimensional electrons gas controls switch of the resonation modes of the modulation unit, and thus realizes dynamic phase modulation of the spatial transmitted terahertz wave. Specifically, modulation processes are as follows. During modulation, a negative voltage is applied to the negative electrode 4 connected to the gate, and a positive voltage is applied to the positive electrode 3 connected to the source, wherein when a difference between the positive voltage and the negative voltage is 0, the HEMT is switched on, and the source resonator and the drain resonator connect with each other through the HEMT as a whole. Referring to FIG. 5, when no voltage is applied, a LC resonation mode (mode I) and a dipole resonation mode (mode II) coexist and couple with each other, wherein an electric field is mainly distributed at the upper metal latitudinal bar and the lower metal latitudinal bar. Referring to FIG. 6, a resonant frequency under such situation is 0.28 THz. When the difference between the positive voltage and the negative voltage is 4-10V, the 2-dimensional electrons gas in the HEMT between the source and the drain is depleted, the HEMT is in a switch-off state, wherein the source resonator and the drain resonator are disconnected and work independently, which forms a mode III with separate upper and lower portions, which is similar to dipole resonation. The electric field is concentrated at a center of the resonance unit as shown in FIG. 6, Referring to FIG. 6, the resonant frequency under such situation is 0.39 THz. The drawings only show surface current distribution on the left side of the resonance unit, and the current distribution on the right side is symmetric due to a symmetric structure of the resonance unit. When the difference of the external voltage is gradually increased from 0, the concentration of the 2-dimensional electrons gas in the HEMT gradually decreases until it is depleted, and the resonance unit gradually switches from a couple state of the mode I and II to an independent state of the mode III, wherein a resonant peak value gradually shifts and a phase different value of the terahertz wave also gradually increases. FIGS. 6 and 7 respectively provide 3-dimensional simulation results of amplitudes and phase transmission curves of the phase modulator when the HEMT is switched on or off. Referring to FIG. 7, within a frequency band of 0.28-0.39 THz, the phase modulator can reach a phase modulation depth of more than 90 degrees, and a maximum phase modulation depth is up to about 140 degrees. It should be known that by changing resonance unit structure parameters, the bandwidth, the frequency band and the modulation depth of the phase modulation are able to be adjusted the size of the. Referring to the method, a bandwidth with the modulation depth of more than 90 degrees is above 0.2 THz.

Figure 8:
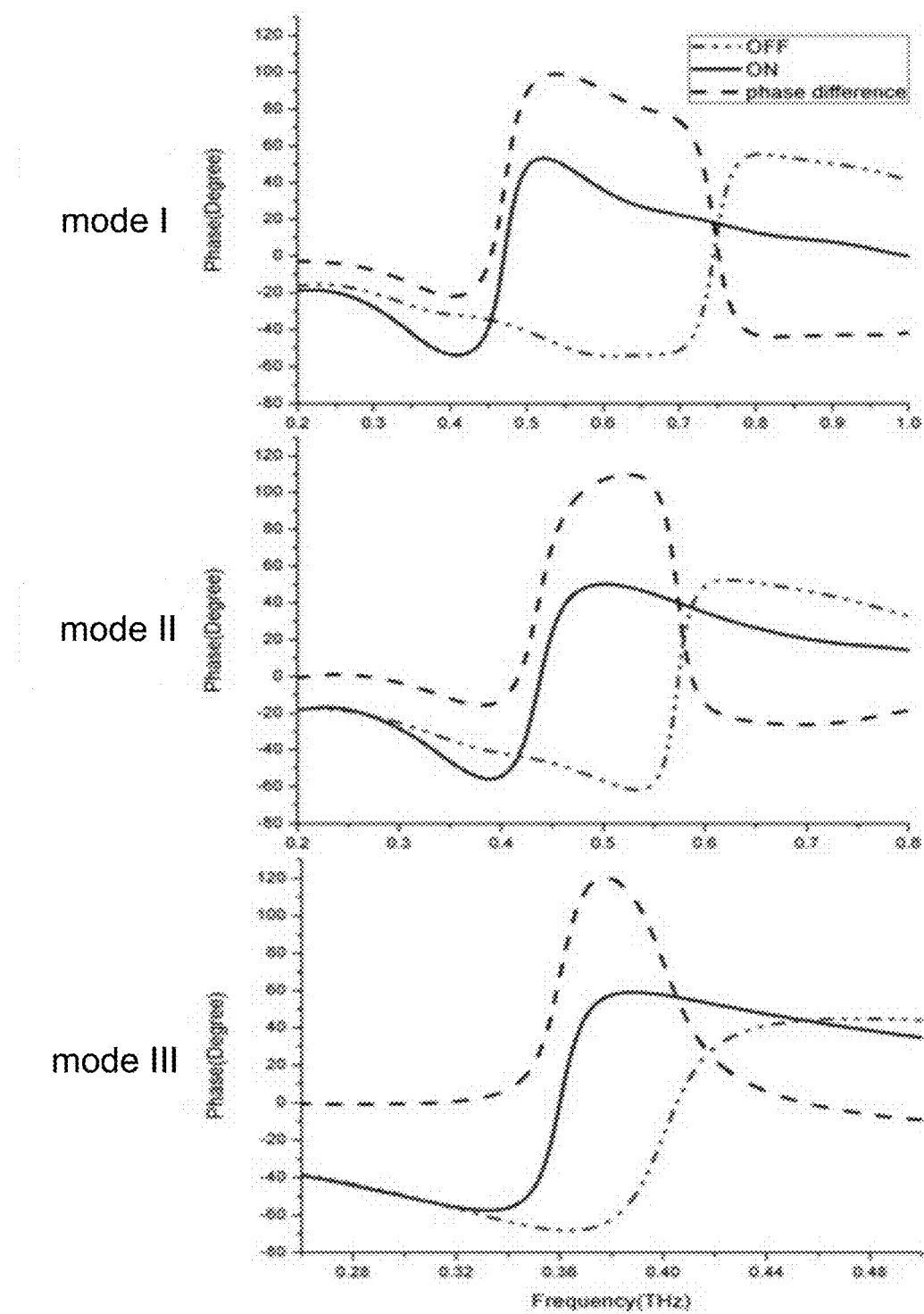
FIG. 8 is experimentally measured phase diagrams of different types of HEMT phase modulators while the transistor is switched on or off.

The Spatial Terahertz wave phase modulator based on the High electron mobility not only obtains a sufficient simulation result by 3-dimensional electromagnetic simulation software, but also is feasibility-proved by experiments. Referring to FIG. 8, a solid line represents the phase transmission curve of the HEMT in the switch-on state, a dotted line indicates the phase transmission curve of the HEMT in the switch-off state, and a broken line indicates the phase modulation depth. Referring to FIG. 8, different phase modulators have different modulation bandwidths, but the modulation depths are all able to reach more than 90 degrees. Therefore, according to actual demands, different HEMT-based phase modulators can be manufactured by changing phase modulator parameters (such as a metal ring radius).

In summary, the HEMT-based terahertz wave space phase modulator is highly practical, which works at THz band with high-speed electronic control, a large modulation depth, and a large bandwidth.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A spatial terahertz wave phase modulator based on a high electron mobility transistor, comprising: a semiconductor substrate; an epitaxial layer on the semiconductor substrate; and a modulation unit array, a positive electrode, as well as a negative electrode on the epitaxial layer; wherein each modulation unit in the modulation unit array comprises: a source resonator, a drain resonator, a gate connector, and a semiconductor doped heterostructure; wherein the drain resonator and the source resonator are structurally identical; comprising: a metal semi-circle and a T-shaped metal feeder; wherein the T-shaped metal feeder comprises a latitudinal branch and a longitudinal branch; the longitudinal branch of the T-shaped metal feeder passes through the metal semi-circle from a top portion thereof; semi-circle openings of the drain resonator and the source resonator face each other and are symmetrically arranged at two sides of the gate connector; the semiconductor doped heterostructure is placed at bottom portions of semi-circle rear ends of the drain resonator and the source resonator, so as to connect the drain resonator and the source resonator; the semiconductor doped heterostructure is also placed at a bottom portion of the gate connector; a row of array elements of the modulation unit array shares the gate connector, and the gate connector of each row is connected to the same negative electrode; the latitudinal branch of the T-shaped metal feeder of the drain resonator of each the modulation unit in a row is connected to the positive electrode in sequence; the latitudinal branch of the T-shaped metal feeder of the source resonator of each the modulation unit in the row is connected to the positive electrode in sequence.

2. The spatial terahertz wave phase modulator based on the high electron mobility transistor, as recited in claim 1, wherein rear ends of the drain resonator and the source resonator are connected to the semiconductor doped heterostructure through a metal electrode.

3. The spatial terahertz wave phase modulator based on the high electron mobility transistor, as recited in claim 1, wherein a short branch extending towards a circle center is respectively arranged at the semi-circle rear ends of the drain resonator and the source resonator.

4. The spatial terahertz wave phase modulator based on the high electron mobility transistor, as recited in claim 2, wherein a short branch extending towards a circle center is respectively arranged at the semi-circle rear ends of the drain resonator and the source resonator.

5. The spatial terahertz wave phase modulator based on the high electron mobility transistor, as recited in claim 1, wherein a portion of the gate connector, which is placed on the semiconductor doped heterostructure, is narrower than other portions of the gate connector.

6. The spatial terahertz wave phase modulator based on the high electron mobility transistor, as recited in claim 1, wherein the semiconductor doped heterostructure are made of AlGaN/GaN, InGaN/GaN, AlGaAs/GaAs, AlGaAs/InGaAs, or AlGaAs/InGaAs/InP, wherein a slash represents combining two materials.

7. The spatial terahertz wave phase modulator based on the high electron mobility transistor, as recited in claim 1, wherein the semiconductor substrate is made of sapphire, high-resistivity silicon, or SiC.

8. The spatial terahertz wave phase modulator based on the high electron mobility transistor, as recited in claim 2, wherein the metal electrode is made of Ti, Al, Ni or Au.

9. The spatial terahertz wave phase modulator based on the high electron mobility transistor, as recited in claim 1, wherein the drain resonator, the source resonator and the T-shaped metal feeder are made of Au, Ag, Cu or Al.

* * * * *